United States Patent [19]

Dutertre

[11] Patent Number: 5,102,524

[45] Date of Patent: Apr. 7, 1992

[54] MULTIPLE ELECTROPHORESIS DEVICE FOR THE CONTROLLED MIGRATION OF MACROMOLECULES THROUGH RECTANGULAR GEL PLATES

[75] Inventor: Bernard Dutertre, Neuilly sur Seine, France

[73] Assignee: Bertin & Cie, Cedex, France

[21] Appl. No.: 477,903

[22] PCT Filed: Sep. 4, 1989

[86] PCT No.: PCT/FR89/00441

§ 371 Date: Apr. 30, 1990

§ 102(e) Date: Apr. 30, 1990

[87] PCT Pub. No.: WO90/02601

PCT Pub. Date: Mar. 22, 1990

[30] Foreign Application Priority Data

Sep. 6, 1988 [FR] France ................................ 88 11626
Nov. 23, 1988 [FR] France ................................ 88 15246

[51] Int. Cl.⁵ .................... B01D 61/42; B01D 57/02; C25B 1/00
[52] U.S. Cl. ............................. 204/299 R; 204/180.1; 204/182.8
[58] Field of Search ...................... 204/299 R, 182.1

[56] References Cited

U.S. PATENT DOCUMENTS 4,088,561  5/1978  Anderson ....................... 204/299 R
4,655,898  4/1987  Poulhes et al. ................. 204/299 R
4,994,166  2/1991  Fernwood et al. ............. 204/299 R

FOREIGN PATENT DOCUMENTS

WO84/02001  5/1984  PCT Int'l Appl. .

Primary Examiner—John Niebling
Assistant Examiner—Caroline Koestner
Attorney, Agent, or Firm—Lowe, Price, LeBlanc & Becker

[57] ABSTRACT

A multiple electrophoresis method and device are disclosed for the controlled migration of macromolecules in gel plates stacked in a direction perpendicular to their plane, at least one series of electrodes (20) disposed at the intersections of two series of perpendicular planes, some perpendicular to the plates (12) and to the desired direction of migration of the macromolecules, the others perpendicular to the first and parallel to the plates (12), the electrodes being connected together selectively and controlled so as to provide both separation of the macromolecules in the plate (12) then transfer thereof to the membranes (22) associated with the plates (12).

19 Claims, 6 Drawing Sheets

MULTIPLE ELECTROPHORESIS DEVICE FOR THE CONTROLLED MIGRATION OF MACROMOLECULES THROUGH RECTANGULAR GEL PLATES

The invention relates to a multiple electrophoresis method and device ensuring the controlled migration of macromolecules in rectangular gel plates.

Techniques are used at the present time for separating macromolecules, such as proteins or nucleic acids, by electrophoresis using an electric field applied to the longitudinal ends of a rectangular plate of an appropriate gel, for example agarose or polyacrylamide. Samples of macromolecules, for example nucleic acids, to be separated are deposited in wells formed in the gel, along an edge of the plate then the whole is immersed in an appropriate electrophoresis liquid. The electrodes placed against said edge of the plate and the opposite edge thereof are connected to different potentials so that an electric field is created between the electrodes in a direction corresponding to the desired direction of migration of the macromolecules in the gel plate. Under the effect of the electric field, the macromolecules of the samples housed in the wells move towards the opposite edge of the plate, through the gel, at speeds which depend particularly on their molar mass so that, at the end of a given time, macromolecules of different molar masses have travelled through the gel over different distances.

In a known technique, the macromolecules thus separated are then transferred either by suction, or by means of an electric field oriented perpendicularly to the plate in the desired direction, on a membrane placed on a large face of the gel plate, for hybridization and subsequent detection thereof.

This technique and the apparatus which has been devised for implementing it relate essentially to the laboratory, i.e. it is a question of small-sized apparatus operating at a slow rate, processing the gel plates one after the other, etc.

Furthermore, the separations obtained with such apparatus are not perfectly repetitive and may vary from one plate to the other or from one sample to the other in the same plate, if only because the electric field developed between the two electrodes is not uniform, because of the heterogeneity of the medium passed through, so that identical macromolecules, having the same molar mass, may migrate over different distances if they are placed at different points on the same plate or on different plates.

The result is particularly difficulties in interpreting the results and the impossibility of automating the apparatus for macromolecule separation by electrophoresis.

The object of the invention is in particular to avoid such drawbacks of the prior technique.

It provides a multiple electrophoresis method and device for separating macromolecules in gel plates in a way which is reliable, faithful, repetitive and perfectly automatable.

Yet another object of the invention is a method and device of this type which make it possible to process simultaneously a large number of gel plates.

A further object of the invention is a method and device of the above type, making it possible to modify at will the conditions of separation of the macromolecules, particularly by controlled variation of the electric field applied to the gel plates for migration of the macromolecules.

For this, the invention provides a multiple electrophoresis method ensuring the controlled migration of macromolecules in rectangular gel plates, characterized in that it consists:

in stacking several plates perpendicularly to their plane while holding them spaced apart so as to form at least a parallelepipedic stack, disposing between the plates and/or in the vicinity of the faces of this stack a plurality of elongate electrodes, for example in the form of wires, parallel to each other and to the planes of the plates, and contained in a series of planes perpendicular to a common desired migration direction of the macromolecules in the plates, immersing the assembly of plates and electrodes in a bath of an appropriate electrophoresis liquid, bringing the electrodes contained in the same plane perpendicular to the migration direction to the same potential, and controlling in space and/or in time the potential differences between the different planes so as to create in the bath and in the plates an electric field whose direction is at all points substantially parallel to the desired migration direction.

The electrodes contained in planes perpendicular to the desired migration direction of the macromolecules define equipotential surfaces which are substantially flat, at least in a first approximation, since they are defined by parallel and coplanar straight lines.

Since the electric field is necessarily perpendicular to the equipotential surfaces, which are themselves perpendicular to the desired migration direction, an electric field is thus necessarily obtained in the gel plates which is oriented in the desired direction, at least at the level of each electrode, despite the heterogeneity of the medium subjected to the electric field.

The result is control of the amplitude and of the orientation of the electric field in the gel plates, which is such that, under identical conditions, perfectly repetitive macromolecule separation and measurements can be obtained.

This offers then the possibility of automating the macromolecule separation processes and controlling them by computer, for example by means of an automaton described in another patent application of the Applicant filed on the same day.

According to another characteristic of the invention, the electrodes are disposed at the intersections of said planes with another series of planes perpendicular to a second desired migration direction, this second direction being perpendicular to the first one and the method consists in controlling successively the potentials of the electrodes in the planes of the first series, then those of the electrodes in the planes of the other series, so as to cause the macromolecules to migrate in said plates successively in the said first direction then in the second.

Thus, it is possible not only to cause separation of the macromolecules in the gel plates but also their transfer on to appropriate membranes placed along one of the large faces of the gel plates.

The method of the invention comprises the creation, by uniform distribution of potential over the electrode planes evenly spaced apart with respect to the stack of plates, of a uniform electric field through the plates of the stack.

The method according to the invention also includes variation of the amplitude and/or of the direction of the electric field through the plates of the stack, by varying the potential distribution in the electrode planes.

The variations in time of the potential differences between the electrode planes may be synchronous and equal to each other, so as to cause the amplitude of the electric field to vary in time without modifying its distribution in space, or else the potential differences between electrode planes may be modified locally, so as to cause the intensity of the electric field to vary locally.

The method of the invention further includes the modification, cyclic or not, of the potential differences between the electrode planes.

Thus, the macromolecules may be caused to migrate intermittently in a desired migration direction.

According to yet another characteristic of the invention, the method also consists in disposing at least two stacks of plates side by side, while juxtaposing them in a direction parallel or perpendicular to said migration direction.

Thus the gel plates of the different stacks may be processed by means of different electric fields.

The invention further provides a multiple electrophoresis device for the controlled migration of macromolecules in gel plates, comprising a tank receiving the gel plates, electrodes adapted for creating an electric field in the gel plates and means for feeding an appropriate electrophoresis liquid into the tank and removing it, characterized in that said device comprises:

support means receiving at least one stack of gel plates and holding them spaced apart from each other, a series of electrodes parallel to each other and to the plates of the stack, disposed in planes perpendicular to a desired migration direction of the macromolecules through the plates, means for electric connection between electrodes in the same plane, for maintaining them in particular at the same potential, means for connection between electrodes of different planes, for maintaining in particular a potential difference between two consecutive planes, means for applying a potential at least to the electrodes situated in end planes between which the stack of plates is disposed, and control means for causing the distribution of the potentials of the electrodes of said planes to vary in space and/or in time.

Preferably, the electrodes will be spaced evenly apart between the ends of the gel plates, as well as between these plates.

The electrodes are disposed at the intersections of two series of planes, the first being perpendicular to the plates and to the desired migration direction, the second being perpendicular to the first and parallel to the plates.

According to another characteristic of the invention, the connection means between two consecutive electrodes of the same plane are of the controlled electric conduction type, variable between a conduction state with substantially zero resistance and at least a conduction state with resistance of a predetermined non zero value.

These connection means may in particular be electronic components, such as transistors, thyristors, etc. which are selectively enabled or disabled.

These connection means may be controlled individually or in groups and preferably by means which are common to all the electrodes situated in the same group of parallel planes.

In one embodiment of the invention, the connection means between electrodes and the control means are carried by at least one plate of dielectric material, on which the electrodes are fixed by one of their ends.

According to another characteristic of the invention, the support is intended to receive at least two stacks of plates disposed side by side and juxtaposed in at least one direction parallel to their planes, and in that a series of electrodes of said type comprising said control means and connection means between electrodes is associated with each stack of plates, for creating in the plates of the different stacks electric fields which are identical or different, as desired, linked to or independent of each other.

In a preferred embodiment of the invention, said electrodes are integrated in a mobile basket forming the support for the gel plates. In practice, it is sufficient to combine these electrodes together by means of plates, perforated or not, or dielectric material grids so as to have a support basket, between the electrodes of which the gel plates may be disposed and which will be immersed in the tank and removed from the tank by the horizontal face thereof.

The invention also provides for the ends, for example the lower ends, of said electrodes to comprise means for coupling or connection to electrodes carried by the corresponding wall, for example, the bottom wall of said tank.

In this case it is then sufficient to place the basket on the bottom of the tank so that the vertical electrodes of the basket may be connected to potential application means and circuits controlling the device, via electrodes at the bottom of the tank.

Advantageously, these coupling or connection means also form means for positioning the basket in the tank.

Preferably, the electrodes of the bottom of the tank are substantially pinpoint and form a square or rectangular mesh network with sides respectively parallel and perpendicular to the desired migration direction for the macromolecules.

They are connected together by controlled connecting means, making it possible selectively to maintain the electrodes situated in the same plane perpendicular to the desired migration direction of the macromolecules at the same potential and so create a potential difference between such successive planes.

In this case, the invention also provides for the vertical walls of the tank to comprise vertical linear electrodes, also connected to controlled connection means making it possible to selectively create potential differences therebetween or else to place them at the same potential.

In order to increase the processing capacity of the device of the invention, the basket may contain, at the same level, at least two series of gel plates disposed head to tail, i.e. in which the plates of one series are substantially in the extension of the plates of the other series, but oriented longitudinally in an opposite direction, with respect to the initial position of the macromolecules.

Thus several double series of gel plates may be processed without increasing the total potential difference in the tank beyond that required for a plate.

The invention also provides for the vertical electrodes of the basket to be surrounded by cylindrical sleeves or tubes of a dielectric material, which are perforated or porous with respect to the electrophoresis liquid.

These tubes, open at their ends, form traps for the gas bubbles produced by electrolysis in contact with the electrodes and guide the bubbles towards the free surface of the liquid, without them coming into contact with the gel plates.

In the following description, given by way of example, reference is made to the accompanying drawings in which.

Figure 1:
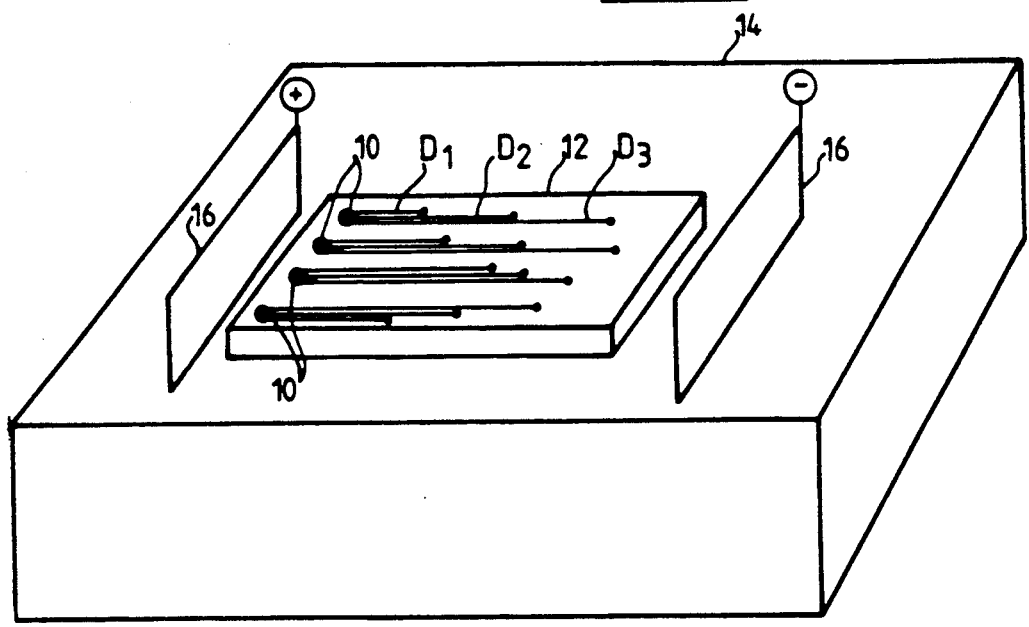
FIG. 1 shows schematically a known apparatus for the separation of macromolecules by electrophoresis.

In FIG. 1, the principle of the separation of macromolecules in a gel plate by electrophoresis has been shown very schematically.

Samples containing macromolecules, for example nucleic acids, are deposited in wells 10 formed in a rectangular plate 12 of an agarose or polyacrylamide gel, along one of the small sides of this plate. The gel plate 12 containing the samples is disposed in an electrophoresis tank 14 between two electrodes 16 (respectively an anode and a cathode), in the position shown in FIG. 1. The tank 14 is then filled with an appropriate electrophoresis liquid, then the electrodes 16 are connected to the terminals of an electric power source, so that a predetermined potential difference is provided between the electrodes, creating an electric field going from one electrode to the other in the desired migration direction of the macromolecules contained in wells 10, through the gel plate 12.

The speeds of migration of the macromolecules through plate 12, towards the opposite edge of this plate, depend on their molar mass; consequently, after a given time, the macromolecules will have travelled through plate 12 by distances which depend on their molar mass. By way of example, distances D1, D2, D3 have been shown travelled over by macromolecules from a well 10.

Such separation of the macromolecules as a function of their molar mass makes it possible, after transfer to a membrane and marking by hybridization or another method, to identify and recognize the macromolecules marked by means of appropriate probes.

The applications of such a technique are multiple and interest industry more and more. However, known electrophoresis apparatus can only be used in the laboratory and cannot be automated.

The reason is particularly because the medium in which the electric field is created, between electrodes 16, is particularly heterogeneous: it comprises plate 12, the transfer membrane which is located along a large face of plate 12, the electrophoresis liquid in which plate 12 and electrode 16 and the support for plate 12 and the membrane bathe, etc. The electric field between electrodes 16 is therefore not uniform and is not oriented at all points parallel to the desired migration direction of the macromolecules through plate 12. By electrochemical reaction, bubbles are also produced in the electrophoresis liquid in contact with the electrodes, because of the relatively high potential difference between the electrodes 16 and their small area, and these bubbles which break away from the electrodes are likely to hinder or influence the migration of the macromolecules.

As mentioned, the method and device of the invention avoid such drawbacks of the present technique and further make it possible to automate the separation and transfer of the macromolecules by electrophoresis.

The method and device of the invention also make it possible to process simultaneously a large number of gel plates, comprising samples of macromolecules to be separated.

Figure 2:
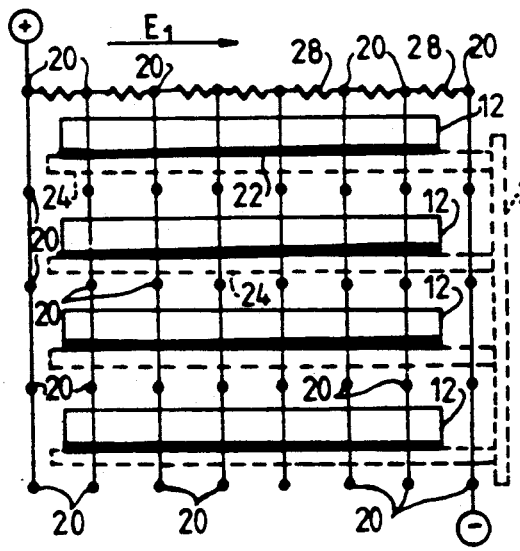
FIG. 2 is a schematic end view of a series of electrodes adapted to be used in a device according to the invention.
Figure 3:
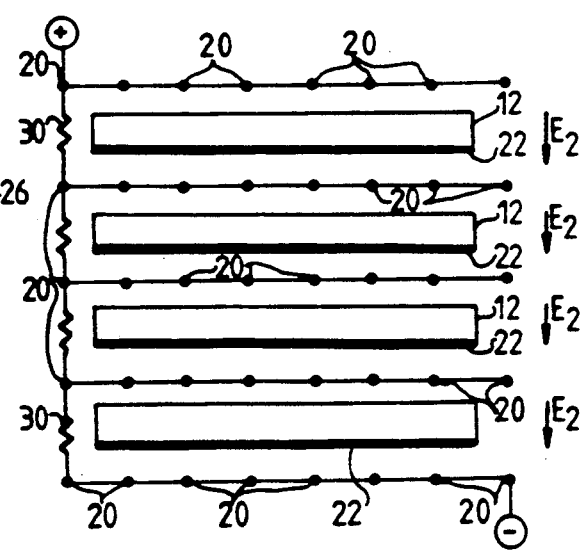
FIG. 3 shows the same series of electrodes, but controlled differently.

Reference will now be made to FIGS. 2 and 3 which illustrate schematically certain essential characteristics of the invention, applicable particularly to the migration of macromolecules through gel plates, and to the transfer of the macromolecules to membranes associated with the gel plates.

The device of the invention comprises essentially, in an electrophoresis tank of appropriate dimensions, a series of elongate electrodes 20 formed for example by wires of an appropriate electrically conducting material. Electrodes 20 are parallel to each other and extend perpendicularly to the plane of the drawing in FIGS. 2 and 3. They are disposed at the intersections of two series of perpendicular planes, some of which are perpendicular to the desired migration direction of the macromolecules and the other are perpendicular to the first ones and to the direction of transfer of the macromolecules on to the membranes.

Electrodes 20, situated in the same plane perpendicular to the desired migration direction, are connected together so as to be at the same potential, whereas the electrodes situated in different planes of this type must be at different potentials, so as to create an electric field parallel to the desired migration direction. Furthermore, the electrodes are connected together, in the desired way, solely at their ends so as to dispose, in the electrode network, a stack of gel plates a large face of which is provided with a transfer membrane 22 and which are carried by supports 24 of a basket 26, shown with phantom lines only in FIG. 2. The gel plates 12 thus form a vertical stack, held spaced apart and are disposed equidistantly or not, as desired, between parallel planes of electrodes 20 so that each passes through a series of perpendicular planes defined by electrodes 20.

One electrode of a vertical end plane, for example the electrode situated at the upper left hand corner in the drawing of FIG. 2, and the diagonally opposite electrode, are connected to two terminals of a DC voltage source, the electrodes situated in the same vertical plane are connected together so as to be at the same potential, and the series of electrodes situated in the same vertical plane is connected to the series of electrodes situated in another adjacent or consecutive vertical plane by an electric resistor 28 of a voltage divider bridge forming therebetween, in steps, a predetermined potential difference. When it is desired to obtain a uniform electric field through all the plates 12, resistors 28 all have the same value and the vertical electrode planes are equidistant.

The vertical parallel planes defined by electrodes 20 are equipotential surfaces, at least at the level of electrodes 20 which they contain. The electric field E1 or potential gradient developed between the electrodes is perpendicular to the equipotential surfaces and is therefore, because of the geometric arrangement of the electrodes and the gel plates 12, parallel at a very large number of points to the desired migration direction of the macromolecules, while having a substantially constant amplitude.

The result is that the results of separation of the macromolecules by migration through the gel plates 12 are faithful and repetitive, at least in a first approximation. Previous calibration or standardization of the device will make it possible, if required, to determine accurately the possible singularities of the electric field which will in any case be small, and to take them into account for evaluating the separation results.

Consequently, the method and device of the invention make it possible to process simultaneously a very large number of gel plates 12.

The same arrangement of electrodes 20 is used in FIG. 3 for transferring the macromolecules to membranes 22 associated with plates 12. With respect to FIG. 2, only the electric connections between electrodes changes, since it is desired to obtain an electric field perpendicular to the planes of plates 12.

For that, the electrodes 20 contained in the same horizontal plane, parallel to plates 12, are connected together so as to be at the same potential, whereas the series of electrodes contained in the same horizontal plane is connected to the series of electrodes contained in another adjacent or consecutive horizontal plane by a resistor 30 of predetermined value. The horizontal planes containing electrodes 20 thus define equipotential surfaces, to which the electric field E2 is perpendicular, which is produced when the upper horizontal plane of electrodes 20 and the lower horizontal plane of electrodes are connected to two opposite terminals of the DC voltage source.

When all the electric resistors 30 have the same value, the electric transfer field has the same amplitude for all the plates 12, whatever their arrangement in the stack.

It is obvious however that it is sufficient to modify the values of resistors 28 and 30 so as to obtain particular electric field distributions through plates 12, in the migration direction and in the transfer direction of the macromolecules. By controlling the values of the potentials applied to the electrodes of the end planes, and varying these potentials in time, it is possible to cause the amplitude of the electric field to vary locally or through the whole of the device, not only permanently but also cyclically. Thus, in particular, it is possible to reverse the direction of the electric field for a given time, then again reverse it so as to re-orient it in the desired migration or transfer direction.

By switching, it is also possible to provide a sweep of a given distribution of potentials applied to successive electrode planes, such distribution comprising particularly reversal of the electric field, which will be caused to move step by step through the network of electrodes.

The successive electrode planes, or some of them, may further be swept by a predetermined potential difference, for example for migration of the macromolecules through the gel plates. Thus, the electric field can be caused to act repetitively on given fractions of the lengths of the gel plates, or on the whole of their length if desired, by creating this field by means of a potential difference several times smaller than the potential difference which it would be necessary to apply to the electrodes situated at the opposite ends of the gel plates so as to obtain an electric field of the same intensity. Important advantages result therefrom, from the point of view of energy consumption, the choice of components for switching the potentials, heating of the liquid, formation of bubbles in this liquid, etc.

Figure 4:
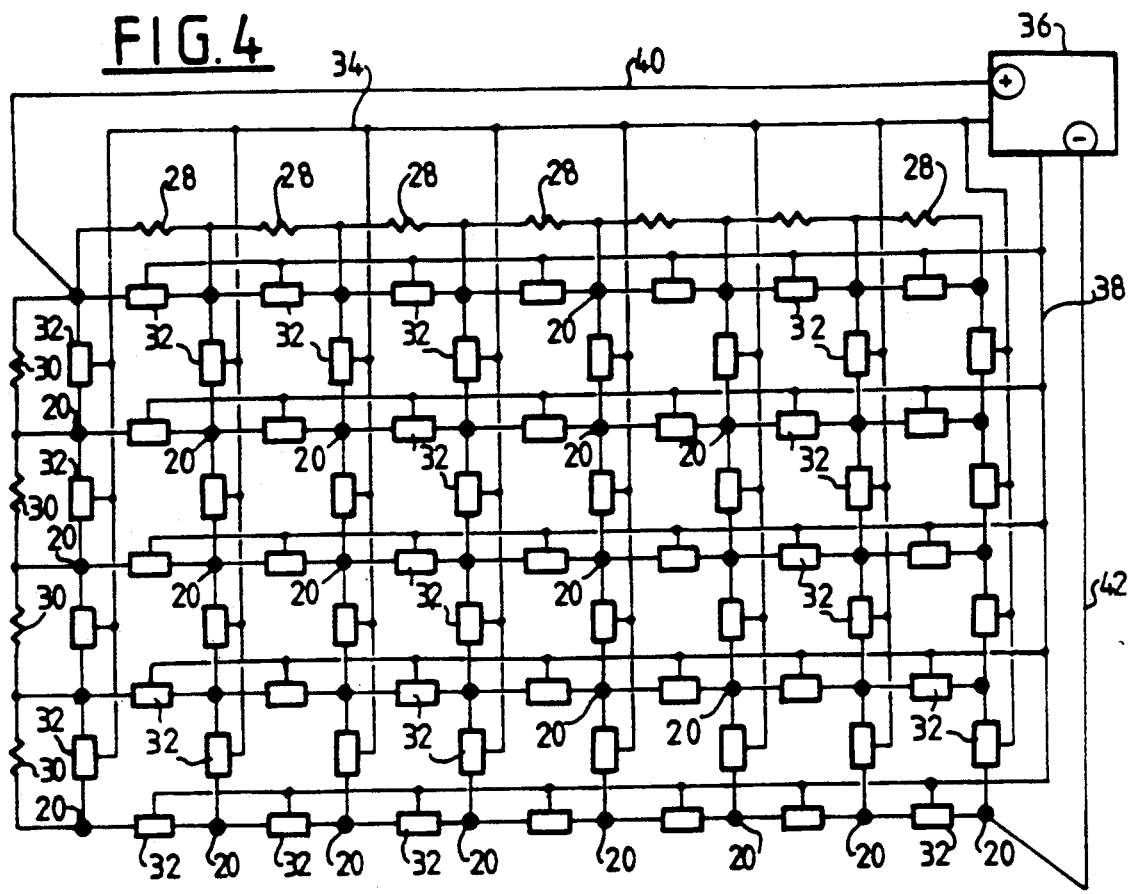
FIG. 4 shows schematically a similar series of electrodes and its control means.

FIG. 4 shows schematically, in an end view, the arrangement of the electrodes and the means for connecting them together for obtaining particularly the arrangements of FIGS. 2 and 3 for the migration and transfer respectively of the macromolecules.

In FIG. 4, each electrode 20 is disposed at the intersection of a horizontal plane and a vertical plane (both perpendicular to the plane of the drawing) and is connected to the adjacent electrodes by a controlled conduction electronic component 32, such as a transistor or a thyristor, which may be selectively enabled and disabled, i.e. whose electric resistance is either substantially zero or substantially infinite.

In the embodiment shown, components 32 connecting together electrodes 20 situated in different horizontal planes, are all connected, by their control input, to the same line 34 connected to a control circuit 36. Similarly, all the components 32 connecting together electrodes 20 situated in consecutive vertical planes, are all connected, by their control input, to the same line 38 connected to the control circuit 36. This circuit also controls the potentials of the electrodes 20 situated at the upper left hand corner and the upper right hand corner of the drawing in FIG. 4, by conducting lines 40 and 42 respectively.

The electrodes contained in the same vertical plane are connected to the electrodes contained in the adjacent vertical plane by a resistor 28, and the electrodes contained in a horizontal plane are connected to the electrodes of the adjacent horizontal plane by a resistor 30, these resistors may have the same or different values, depending on the case. Variable resistors may in particular be used.

When all the components 32 connecting together the electrodes situated in successive horizontal planes are controlled so as to have substantially zero resistance, and when all the components 32 connecting together the electrodes situated in successive vertical planes are controlled so as to have a substantially infinite resistance, the arrangement of FIG. 2 is obtained.

Conversely, when components 32 connecting together the successive horizontal planes are controlled so as to have a substantially infinite resistance and when the components 32 connecting together the successive vertical planes are controlled so as to have a substantially zero resistance, the arrangement of FIG. 3 is obtained.

When resistors 28 and 30 are replaced by variable potential sources, whose value is controlled by an appropriate control circuit such as an operational amplifier, electric fields are obtained which are locally different from one zone of a plate to another.

By means of a control circuit 36, the potentials applied by lines 40 and 42 to the electrodes of the upper left and upper right hand corners of the network of FIG. 4 may be varied as desired. Thus, the electric field may be temporarily reversed, at regular intervals or not, for example so as to obtain a pulsed electric field. The plates may also be swept by a sequence of electric fields which are locally different, even opposite.

Figure 5:
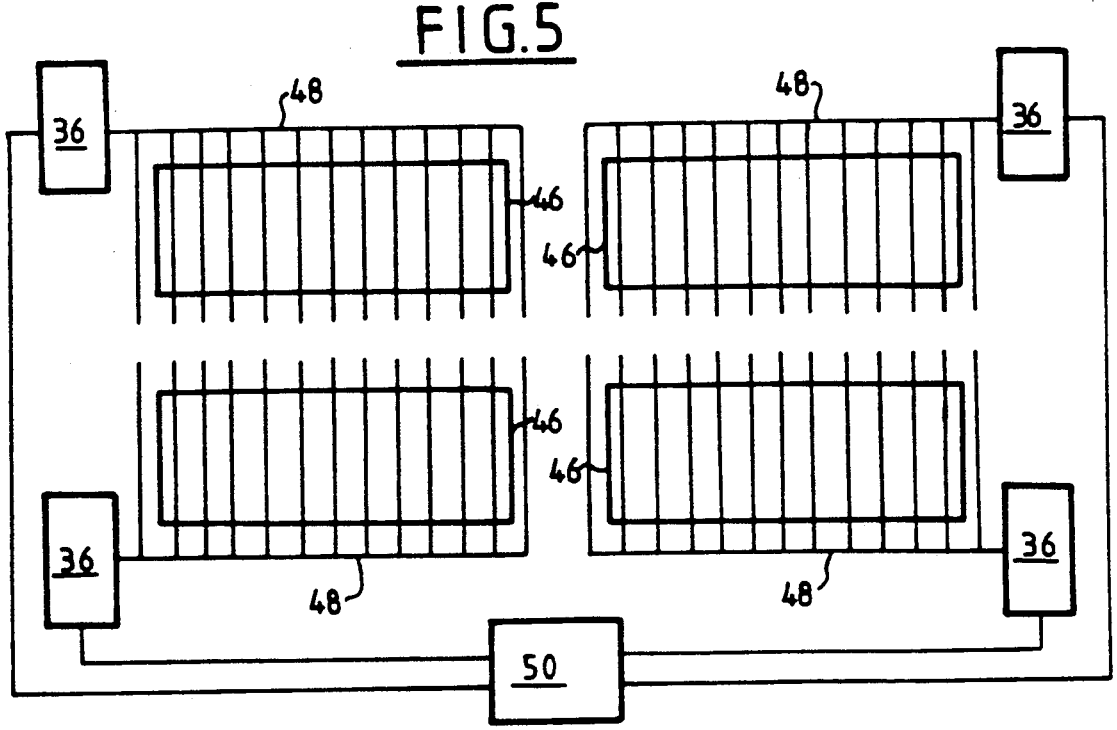
FIG. 5 shows schematically, in a top view, the arrangement of four series of electrodes according to the invention, for four stacks of gel plates.

When series of gel plates are to be subjected to different electric fields, i.e. whose distributions in space and/or variations in time are different, the arrangement shown in FIG. 5 may be used which makes possible the simultaneous processing of a number of stacks 46 of gel plates. Each stack 46 is associated with an electrode system 48 of the same type as that of FIG. 4, comprising a circuit 36 controlling the variations of the electric field through the stack of plates. Each control circuit 36 is itself connected to a central control system 50 which is for example driven by a computer. In this case, the potential variations in the electrode system 48 associated with the different stacks of plates 46 may be as desired identical or different, linked together or independent of each other.

The method and device of the invention thus make it possible to cause separation of macromolecules of different molar masses under uniform conditions, or else to study the behaviour of macromolecules of the same kind and with the same molar mass in different electric fields and in gel plates of different kinds.

An advantage of the electrode arrangement according to the invention is that gel plates may occupy all the positions provided between the electrode planes, or only some of them, without a modification of the distribution of the electric fields resulting therefrom.

Figure 6:
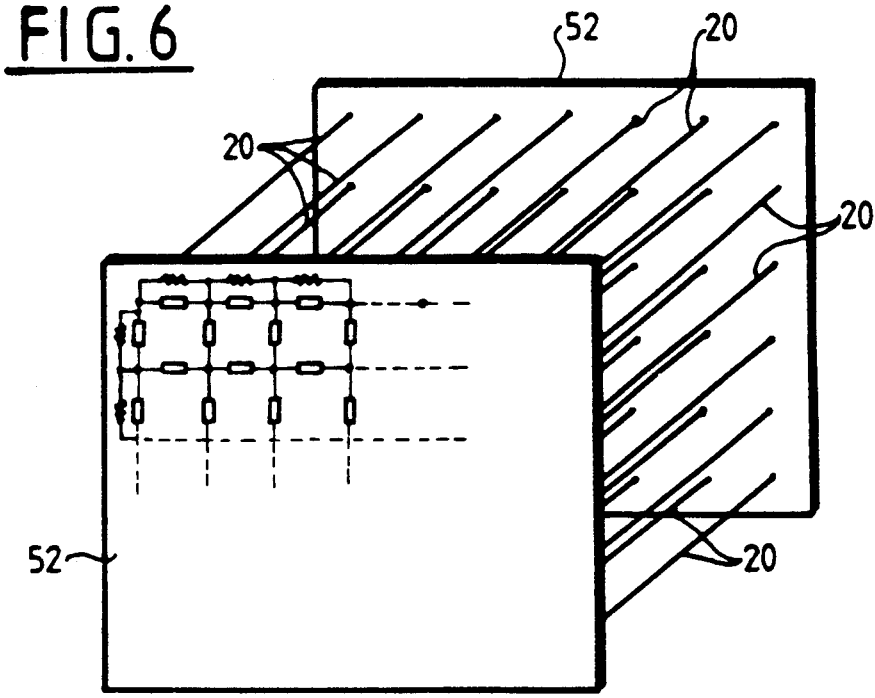
FIGS. 6 and 7 are two schematic perspective views of a network of electrodes in two different embodiments of the invention.

In practice (FIG. 6) the electrodes 20 will all be fixed, by one end, to the same plate 52 of dielectric material including the components 28, 30, 32 and the necessary connections. Since the electrodes will advantageously be conducting material wires, they will be fixed at their other end to a second dielectric material plate which will comprise, or not, some of the required connection components.

The potential source and control circuits 36, 50 will preferably be outside the electrophoresis liquid bath.

As shown schematically in FIG. 2, the different gel plates are mounted on supports forming part of a basket 26, which is movable in translation inside and outside the electrode network.

Figure 7:
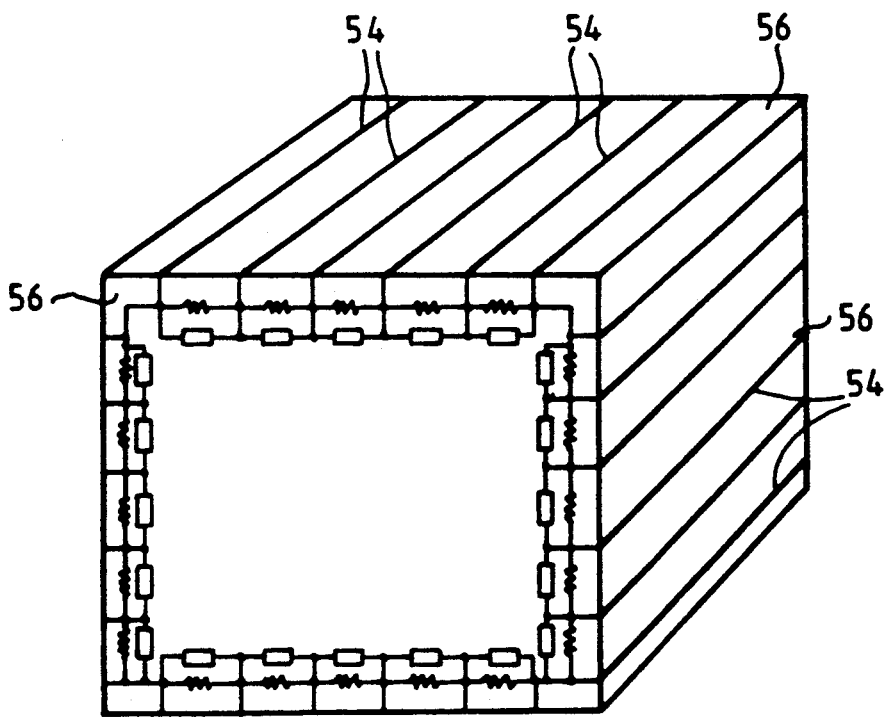

In a variant (FIG. 7), the electrodes may be limited to parallel conducting strips 40 formed on the walls 56 of the tank, for example by metallizations.

The electrophoresis tanks according to the invention are, in a way known per se, equipped with a system for causing the electrolysis liquid to flow and cooling it.

Figure 8:
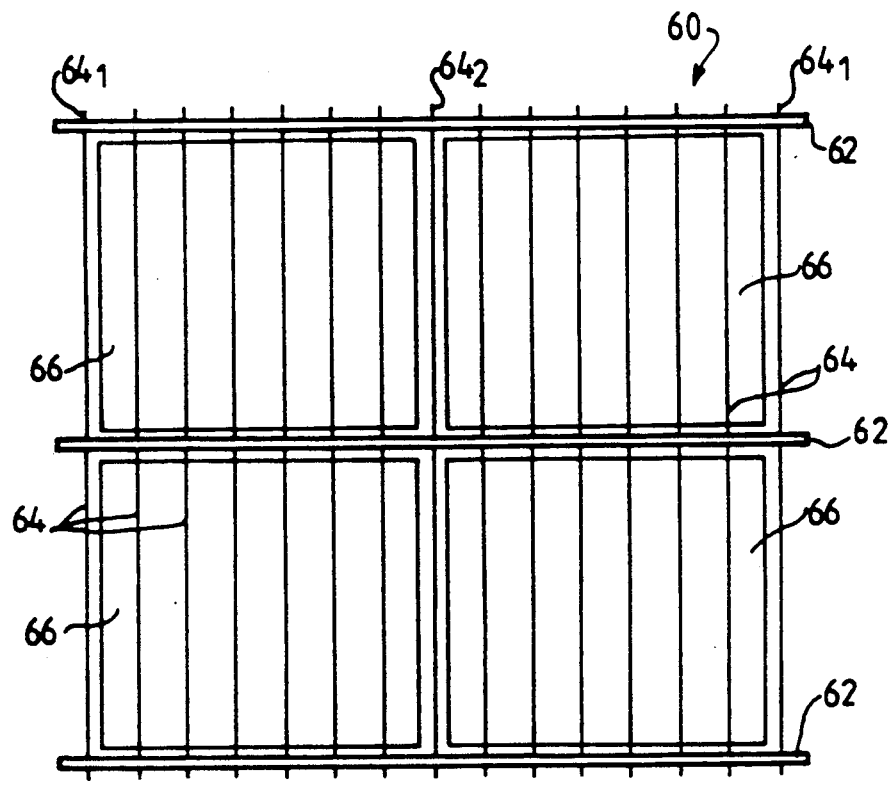
FIG. 8 is a schematic elevational view of a gel plates support basket.
Figure 9:
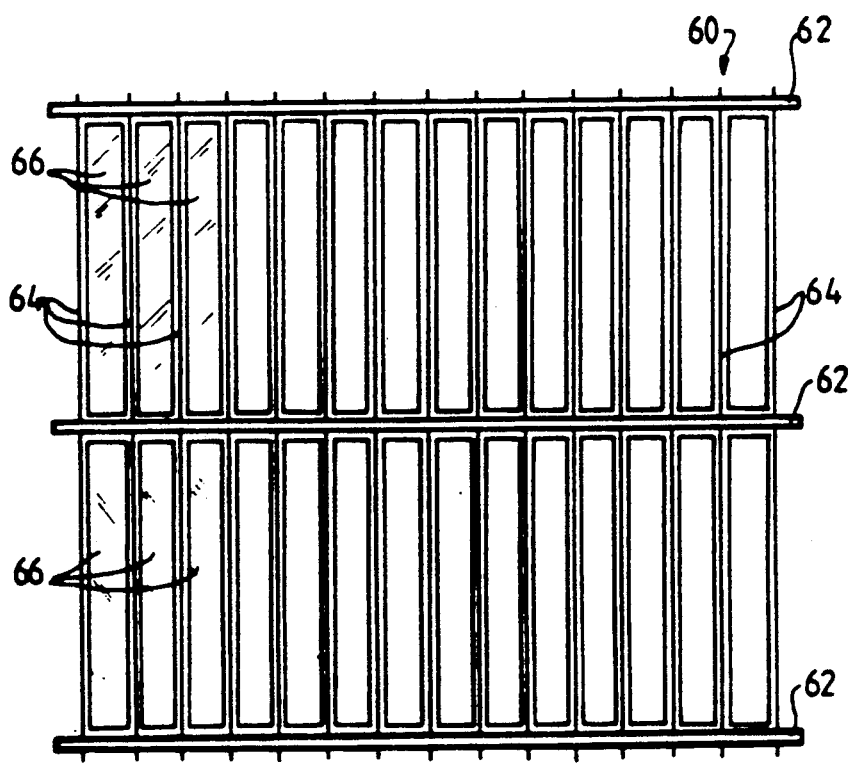
FIG. 9 is a side view of this basket.

Reference will now be made to FIGS. 8 and 9 in which a support basket has been shown schematically for the gel plates according to the invention. Basket 60 comprises essentially horizontal plates 62 superimposed vertically and separated from each other by a distance equal to the height of a vertically disposed gel plate, some plates 62 being set back from the walls of the tank and/or perforated so as to allow the gas bubbles to pass or are even formed by grids.

Plates 62, made from a dielectric material, are connected together by vertical rectilinear electrodes 64 which may be rigid rods of an electrically conducting material, or else simple electrically conducting wires stretched between plates 62, in this case connected together by rigid non electrically conducting uprights, having the desired mechanical strength and disposed for example at the corners and at the centre of plates 62.

Electrodes 64 are disposed in a rectangular or square transverse mesh network the purpose of which is essentially to provide equipotential surface hang-up lines.

The gel plates 66 are disposed vertically on plates 62 between electrodes 64, so that the desired migration direction of the macromolecules through the gel plates is horizontal.

As can be seen in FIGS. 8 and 9, at the different levels of basket 60, a fairly large number of gel plates 66 can be disposed side by side which form, at each level, for example two series of plates, the plates of one series being situated in the extension of the corresponding plates of the other series.

As desired, the plates of one series may be oriented in the same direction as the plates of the other series, or else in the opposite direction. In the first case, the potential difference between the ends of the basket will be about twice the potential difference to be applied at the ends of a gel plate. In the second case, the potential difference between the ends of the basket will be substantially equal to the potential difference between the ends of a gel plate: a voltage $V_1$ will for example be applied to electrodes $64_1$ at the ends of the basket and a voltage $V_2$ to the electrodes $64_2$ in the transverse median plane of the basket, with the difference $V_1-V_2$ equal to the potential difference to be applied between the ends of a gel plate.

Figure 10:
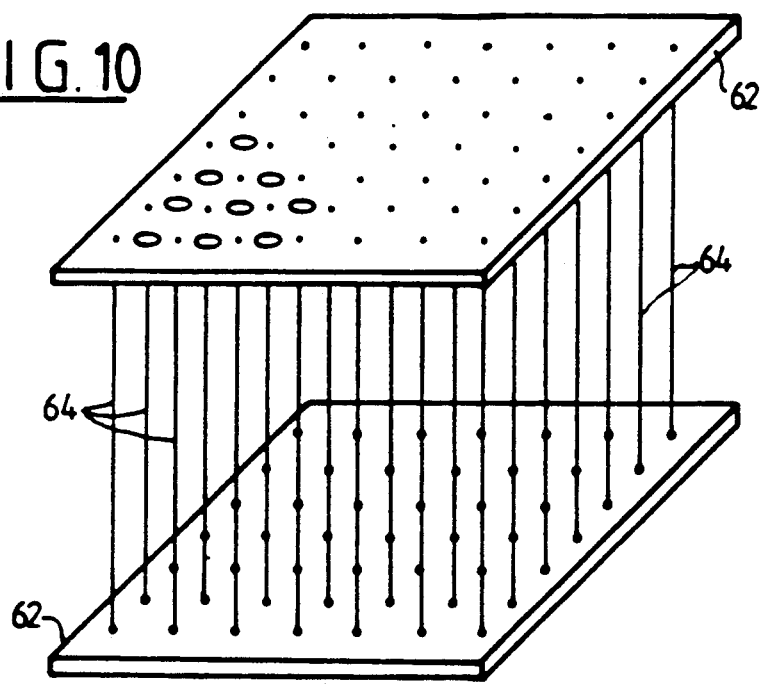
FIG. 10 is a schematic perspective view of a plate support basket.

FIG. 10 is a perspective view of a variant of embodiment of the basket, which only comprises a single loading level for the gel plates, defined between two plates 62 of a dielectric material, only the upper plate of which is perforated to allow the passage of the gas bubbles formed by electrolysis in the electrophoresis liquid.

Figure 11:
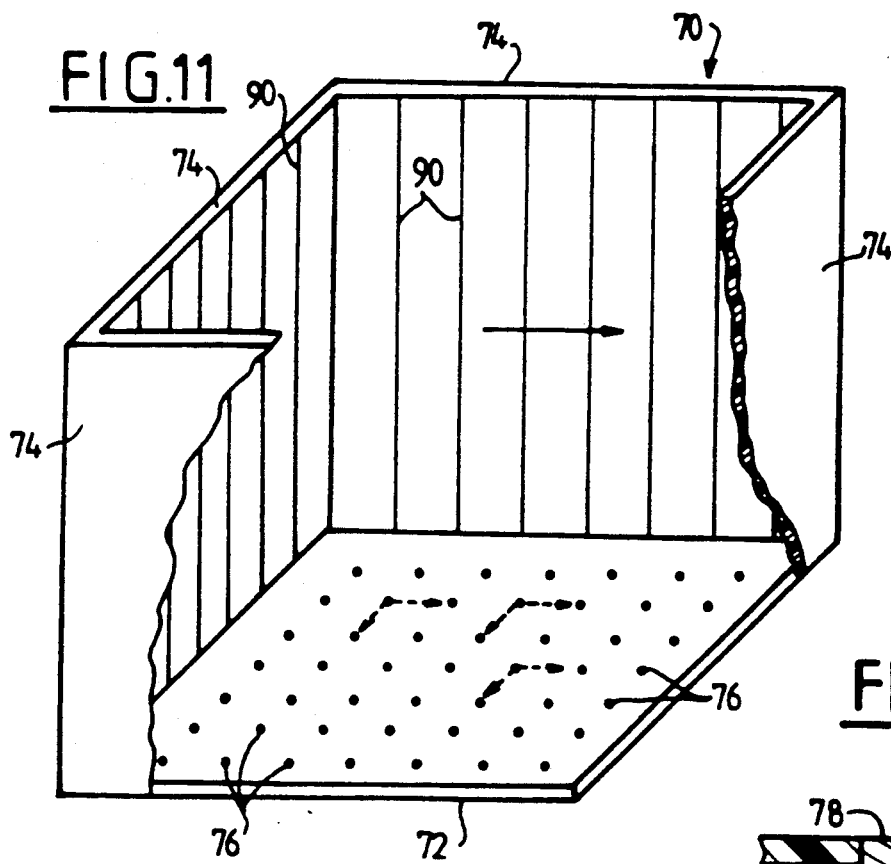
FIG. 11 is a schematic perspective view, with parts cut away, of an electrophoresis tank.

FIG. 11 shows schematically a tank for receiving the basket of FIG. 10.

This tank 70 has a parallelepipedic shape and comprises a horizontal bottom 72 and four vertical walls 74 with possibly an upper mobile horizontal wall, not shown in the drawings.

The bottom 72 of the tank comprises a series of substantially pinpoint electrodes 76 forming a square or rectangular mesh network, identical to that of the electrodes 64 of the basket, so that, when the basket is placed in the tank, the pinpoint electrodes 76 of bottom 62 of the tank are situated exactly in the extension of the vertical electrodes 64 of the basket.

Figure 12:
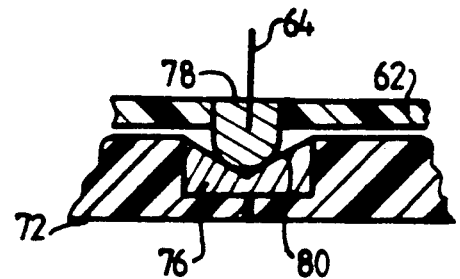
FIG. 12 is a partial view on a larger scale of a means for positioning the basket in the tank.

As shown in FIG. 12, the lower ends of electrodes 64 may comprise means for contact with the pinpoint electrodes and positioning of the basket in the tank.

In the example shown, each wire-shaped electrode 64 of the basket is connected, at its lower end, to a conducting stud 78 having a lower semi-spherical surface projecting from the lower face of the bottom plate 62 of the basket, and which is received in a truncated cone shaped recess 80 of a conducting stud forming a pinpoint electrode 76 at the bottom of the tank.

The pinpoint electrodes 76 are connected together, outside the tank, by the circuit shown in FIG. 13 and already described with reference to FIG. 4, which comprises controlled connecting means between adjacent electrodes 76. The different rows of electrodes 76 are connected together by connecting elements 82 which are conducting with a substantially zero electric resistance, or disabled with a substantially infinite electric resistance Similarly, the different columns of pinpoint electrodes 76 are connected together by connecting elements 84, of the same type as elements 82. Furthermore, resistors 86, or equivalent conducting elements, are provided between the different rows of electrodes 76 and resistors 88, or equivalent conducting elements, are provided between the different columns of pinpoint electrodes 76.

The connecting elements 82 and 84 are controlled in the following way: when the connecting elements 82 have a substantially zero resistance, elements 84 have a substantially infinite electric resistance so that the columns of pinpoint electrodes 76 define equipotential lines and so that two successive columns of electrodes have therebetween a potential difference determined by the value of the corresponding resistor 88, the electrodes at the upper left hand corner and the lower right hand corner of the circuit being connected to appropriate potential sources. Alternately, when the connecting elements 82 have a substantially infinite electric resistance and elements 84 have a substantially zero electric resistance the rows of pinpoint electrodes define equipotential lines and two successive rows have therebetween a potential difference determined by the value of the corresponding resistor 86.

The vertical walls 74 of tank 70 may comprise (FIG. 11) vertical linear electrodes 90, formed for example by metallized lines on their internal surface, which are connected together and to the rows and to the columns respectively of pinpoint electrodes 76 of the bottom of the tank by elements 82, 84.

The operation of tank 70 shown in FIG. 11 will be readily understood. The basket loaded with the desired number of gel plates is placed in the tank and is there positioned automatically, by the means shown in FIG. 12, which at the same time provide the electric connection between the pinpoint electrodes 76 and electrodes 64 of the basket. By controlling the connecting elements 82 and 84, migration of the macromolecules in the gel plates takes place, first of all, parallel to the length of these plates then, by reversing the roles of the connecting elements 82 and 84, migration of the macromolecules occurs through the thickness of the plates and transfer thereof to the associated membranes. The rows, then respectively the columns of pinpoint electrodes 76, as well as the linear electrodes 90 of the vertical faces of the tank, define flat equipotential surfaces making reliable and rigorous measurements possible as already mentioned.

In FIG. 11, the continuous line arrow shows the direction in which the gel plates are oriented and the broken line arrows show the direction of the electric fields, for migration and transfer respectively of the macromolecules.

The movement of the basket in tank 70 takes place by vertical translation, through the open upper face of tank 70, for example by means of a robot arm which brings the basket into a loading-unloading station where a basket can be prepared while another basket is being processed in tank 70.

Figure 13:
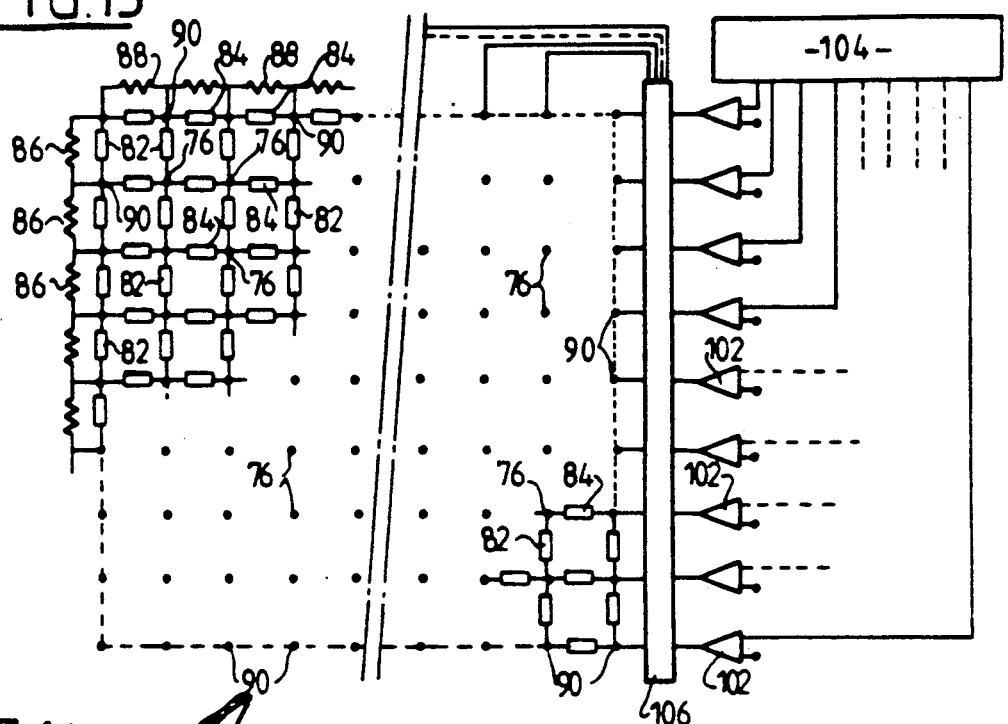
FIG. 13 is a schematic view of the connection circuit for the electrodes at the bottom of the tank.

In a simpler variant shown in FIG. 13, the bottom 92 of the tank comprises pinpoint electrodes 94, disposed in a square mesh square network and comprising rows in which they are connected together by conductors embedded in the bottom of the tank. These rows correspond respectively to the rows of electrodes 64 of a basket and are connected at their ends to vertical electrodes 96 formed on two vertical opposite faces 98 of the tank. These electrodes 94 and 96 define, with the rectilinear electrodes 64 of a basket, equipotential planes which are perpendicular to the desired direction of migration of the macromolecules.

Then, the procedure is as follows: the basket is placed in the tank so that the gel plates which it contains extend perpendicularly to the equipotential planes defined by the linear electrodes 94 and 96. Electrophoresis then causes migration of the macromolecules in the gel plates, parallel to the length of the plates. Then the basket is removed from the tank, rotated through 90° about a vertical axis and then replaced in the tank, so that the gel plates will be parallel to the equipotential planes defined by the linear electrodes 94 and 96. Electrophoresis will then cause migration of the macromolecules in the thickness of the gel plates, and transfer thereof to the associated membranes.

The two broken line arrows show the longitudinal orientations of the gel plates, in the two respective macromolecule migration and transfer positions, and the continuous line arrows correspond to the orientation of the electric field between the electrode planes.

In a variant, two tanks may be provided such as those shown in FIG. 13 disposed in the immediate vicinity of each other, one providing migration of the macromolecules over the length of the gel plates and the other transfer of the macromolecules to the associated membranes.

The other two vertical faces 100 of the tank of FIG. 13 are without electrodes.

To fix the potentials of the different electrode planes, operational amplifiers may be used controlled by a data processing system. It is then very simple to obtain between the electrode planes electric fields which are variable in time and in space, according to cyclic laws or not, to use electric fields of a pulsed type, etc.

For example, as shown in the right-hand part of FIG. 12, operational amplifiers 102 are each connected, at their output, to a row of electrodes 76. One of their inputs is connected to an output of a control circuit 104, whereas their other input is grounded.

When the electrodes 76 form a square network, a multiple switch 106 applies the output voltages of the amplifiers 102 either to the rows or to the columns of electrodes 76.

Figure 14:
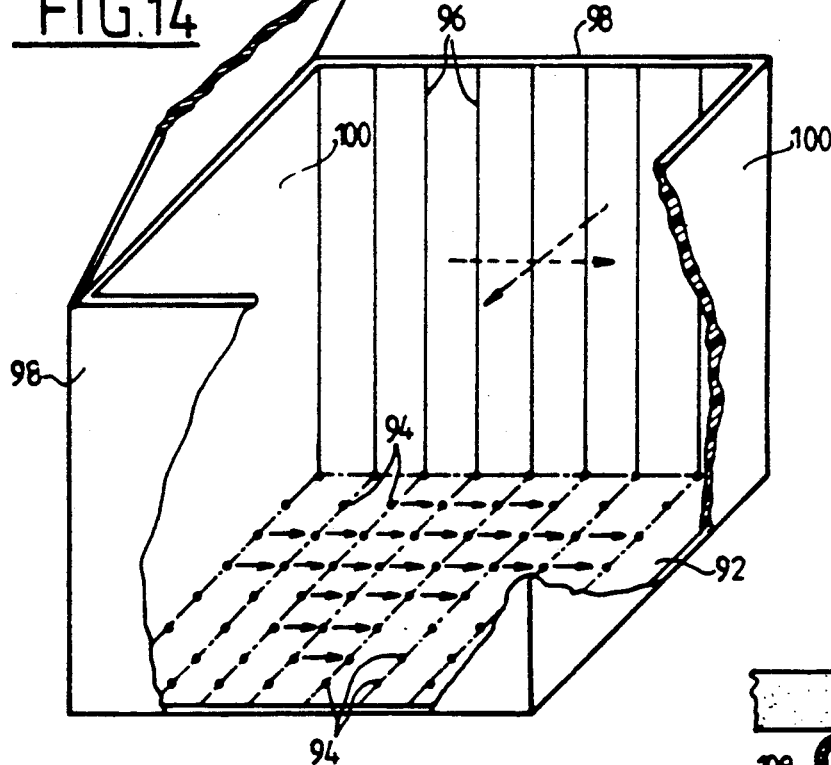
FIG. 14 is a schematic perspective view, with parts cut away, of another embodiment of an electrophoresis tank.
Figure 15:
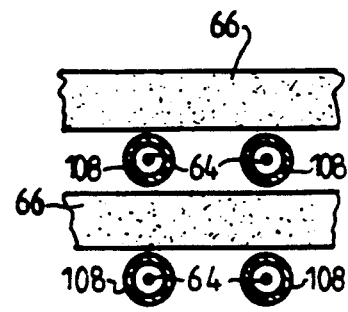
FIG. 15 is a partial schematic view in cross section of porous tubes fitted about vertical electrodes of the basket.

In FIG. 14, cylindrical tubes or sleeves 108 have been shown schematically surrounding the vertical electrodes 64 of a basket. These tubes 108, open at their ends, are made from a dielectric material and are either perforated or porous, to permit passage of the electrophoresis liquid through their wall in the direction of electrodes 64. These tubes thus form bubble traps in which the gas bubbles produced by electrolysis are guided towards the free surface of the liquid, without coming into contact with the gel plates. They also serve for protecting the electrodes 64 and prevent the gel plates 66 from coming into contact with the electrodes. In addition, electrodes may then be used formed from a less costly conducting material than platinum. If deposits are formed by electrolysis in contact with these electrodes, tubes 108 prevent these deposits from passing into the liquid bath in which the gel plates are placed.

In the foregoing, embodiments of the invention have been described which are applicable to the case where, with the gel plates vertical, the two directions of migration and transfer of the macromolecules are horizontal. Of course, the invention also covers the case where, with the gel plates vertical, the direction of migration of the macromolecule in the plates is vertical and their transfer direction to the associated membranes is horizontal. For that it is sufficient to use baskets in which electrodes 64 are horizontal.

I claim:

1. A multiple electrophoresis device for the controlled migration of macromolecules in gel plates, comprising a tank receiving the gel plates and an appropriate electrophoresis liquid,
   support means receiving at least one stack of parallel gel plates and holding them spaced apart from each other in said tank,
   a series of electrodes parallel to each other and to the plates of the stack, disposed in a plurality of planes perpendicular to a desired migration direction of the macromolecules through the plates, at least some of these planes being located between the ends of the gel plates,
   means for electric connection between electrodes in a same plane, for maintaining them at a same potential,
   means for connection between electrodes of different planes, for maintaining a potential difference between two consecutive planes,
   means for applying a potential at least to the electrodes situated in end planes between which the stack of plates is disposed, and
   control means for causing the distribution of the potentials of the electrodes of said planes to vary in space and in time.

2. Device according to claim 1, wherein the electrodes are disposed at the intersections of two series of planes, the planes of the first series being perpendicular to the plates and to the desired migration direction, the planes of the second series being perpendicular to the planes of the first series and parallel to the plates.

3. Device according to claim 2, comprising electric connection means between electrodes contained in a same plane of the second series for bridging them to a same potential, and connection means between electrodes of different planes of the second series for providing a potential difference between these different planes and creating an electric field $E_2$ perpendicular to the plates, defining a second direction of displacement of the macromolecules.

4. Device according to claim 1, wherein the electrodes are spaced apart evenly along the gel plates, and between the gel plates.

5. Device according to claim 1, wherein the connection means between two consecutive electrodes of a same plane are of the controlled electric conduction type, variable between a conduction state with substantially zero resistance and at least a conduction state with resistance of a predetermined non zero value.

6. Device according to claim 5, wherein said connection means are connected to control means which are common to all the electrodes situated in a same group of parallel planes.

7. Device according to claim 1, wherein the means for connection between electrodes and the control means are carried by at least one plate of dielectric material, on which the electrodes are fixed by one of their ends.

8. Device according to claim 1, wherein each gel plate is disposed in the electrophoresis tank between two groups of coplanar electrodes.

9. Device according to claim 1, wherein the support is intended to receive at least two stacks of gel plates disposed side by side and juxtaposed in at least one direction parallel to their planes, and wherein a series of electrodes of the above type comprising said control means and connection means between electrodes is associated with each stack of plates, for creating in the plates of the different stacks electric fields which are identical or different, linked to or independent of each other.

10. Device according to claim 1, wherein said control means are driven by computer.

11. Device according to claim 1, wherein the gel plates are disposed vertically in the tank between said electrodes.

12. Device according to claim 11, wherein the electrodes are bars of a mobile basket forming the support for the gel plates.

13. Device according to claim 12, wherein the lower ends of the electrodes comprise means for connection to electrodes carried by the bottom wall of the tank.

14. Device according to claim 13, wherein the connection means also form means for positioning the basket in the tank.

15. Device according to claim 13, wherein the electrodes of said bottom wall of the tank are substantially pinpoint electrodes.

16. Device according to claim 13, wherein the electrodes of said bottom wall of the tank are substantially pinpoint and connected together by parallel conductors perpendicular to the desired direction of migration of the macromolecules in the gel plates.

17. Device according to claim 13, wherein the vertical walls of the tank comprise linear electrodes perpendicular to the desired direction of migration of the macromolecules and connected to control means for selectively providing potential differences therebetween or placing them at the same potential.

18. Device according to claim 12, wherein said basket contains, at the same level, at least two series of gel plates in which the plates of one series are substantially in the extension of the plates of the other series, and oriented either in the same direction or in an opposite direction.

19. Device according to claim 1, wherein the electrodes are surrounded by cylindrical tubes of a dielectric material, which are perforated or porous and form bubble traps.

* * * * *